United States Patent [19]
Mussi et al.

[11] Patent Number: 5,470,743
[45] Date of Patent: Nov. 28, 1995

[54] TRANSMEMBRANE CELL CULTURE DEVICE

[75] Inventors: Edward F. Mussi, Hewitt; Harry E. Gray, Bloomingdale, both of N.J.

[73] Assignee: Becton, Dickinson and Company, Franklin Lakes, N.J.

[21] Appl. No.: 226,448

[22] Filed: Apr. 12, 1994

Related U.S. Application Data

[63] Continuation of Ser. No. 62,482, May 17, 1993, abandoned, which is a continuation of Ser. No. 924,394, Aug. 3, 1992, abandoned, which is a continuation of Ser. No. 665,383, Mar. 6, 1991, abandoned.

[51] Int. Cl.$^6$ .................................................. C12M 3/06
[52] U.S. Cl. ........................ 435/297.1; 435/297.5; 435/303.1; 435/305.2; 435/287.3; 435/287.8; 435/288.4
[58] Field of Search .................................... 435/284–287, 435/296, 298–301, 310, 311, 809; 422/99, 101, 102, 104

[56] References Cited

U.S. PATENT DOCUMENTS

| | | | |
|---|---|---|---|
| 3,990,852 | 11/1976 | Piazzi et al. | 422/102 |
| 4,308,351 | 12/1981 | Leighton et al. | 435/284 |
| 4,748,124 | 5/1988 | Vogler | 435/240 |
| 4,871,674 | 10/1989 | Matsui et al. | 435/284 |
| 4,959,197 | 9/1990 | Parekh et al. | 422/101 |
| 5,026,649 | 6/1991 | Lyman et al. | 422/101 |

FOREIGN PATENT DOCUMENTS 0334015  9/1989  European Pat. Off. ............... 435/287

OTHER PUBLICATIONS

"Co–Culture of Primary Pulmonary Cells to Model Alveolar Injury and Translocation of Proteins" In Vitro Cell Dev. Biol. 26:1135–1143, Dec. 1990 1990 Tissue Culture Association James B. Mangum, Jeffrey I. Everitt, James C. Bonner, Lynne R. Moore and Arnold R. Brody.

*Primary Examiner*—William H. Beisner
*Attorney, Agent, or Firm*—Nanette S. Thomas

[57] ABSTRACT

A removable cell culture insert support device is provided which allows the initial development of cell cultures on the bottom membrane surface of an inverted cell culture insert. Following successful cell culture development, the support device of the invention is discarded and the conventional insert is reoriented and then suspended in a conventional multi-well plate with the initially developed cells on the bottom surface of the insert membrane. The upper surface of the membrane is then available for developing a second cell type for transmembrane interaction as required. The removable support includes a cup-shaped chamber with a surrounding skirt to accommodate the cell insert of interest, with the removable support having appropriate cooperating attaching surfaces. A double-sided adhesive may be used to temporarily join the two parts together.

2 Claims, 2 Drawing Sheets

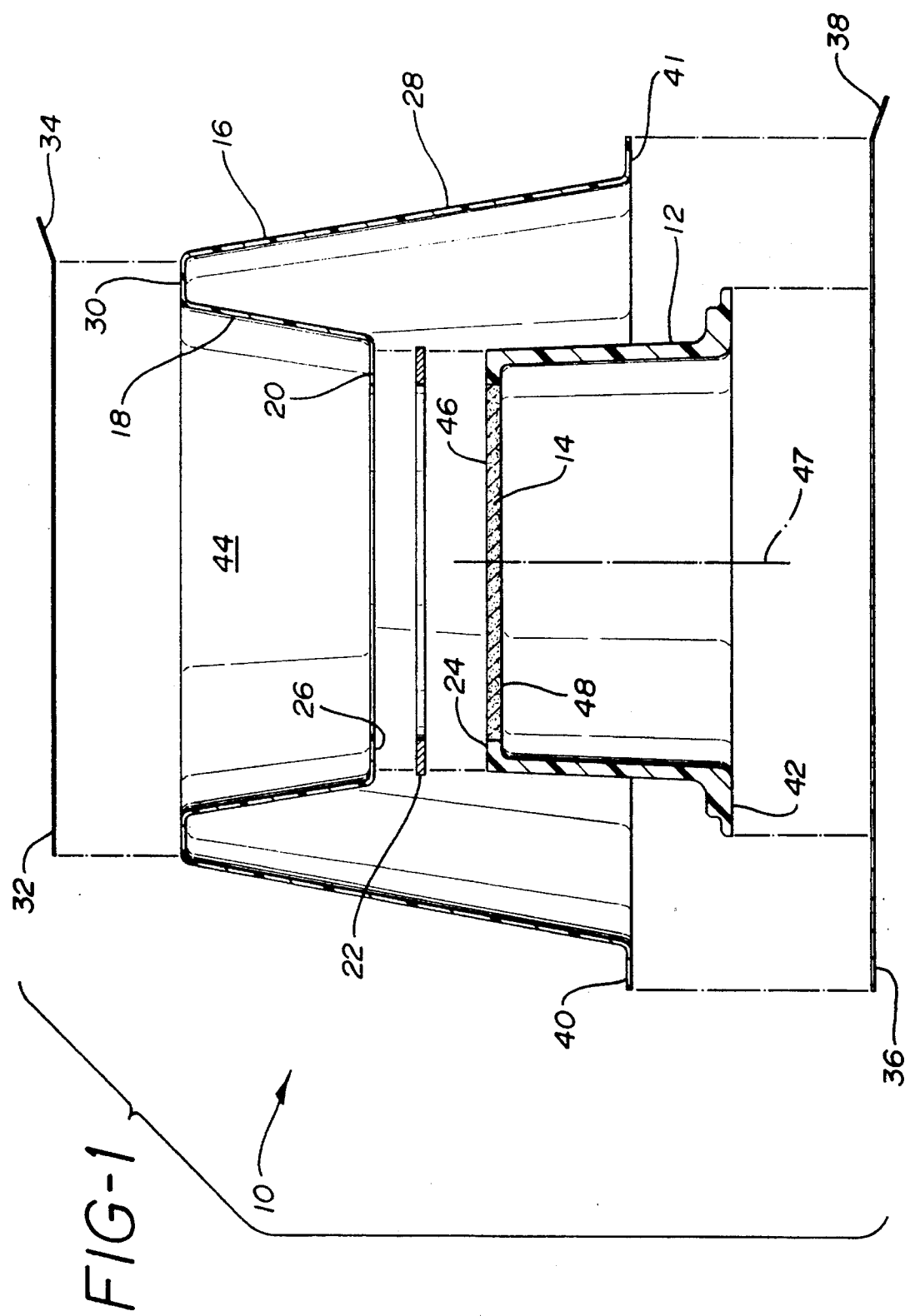

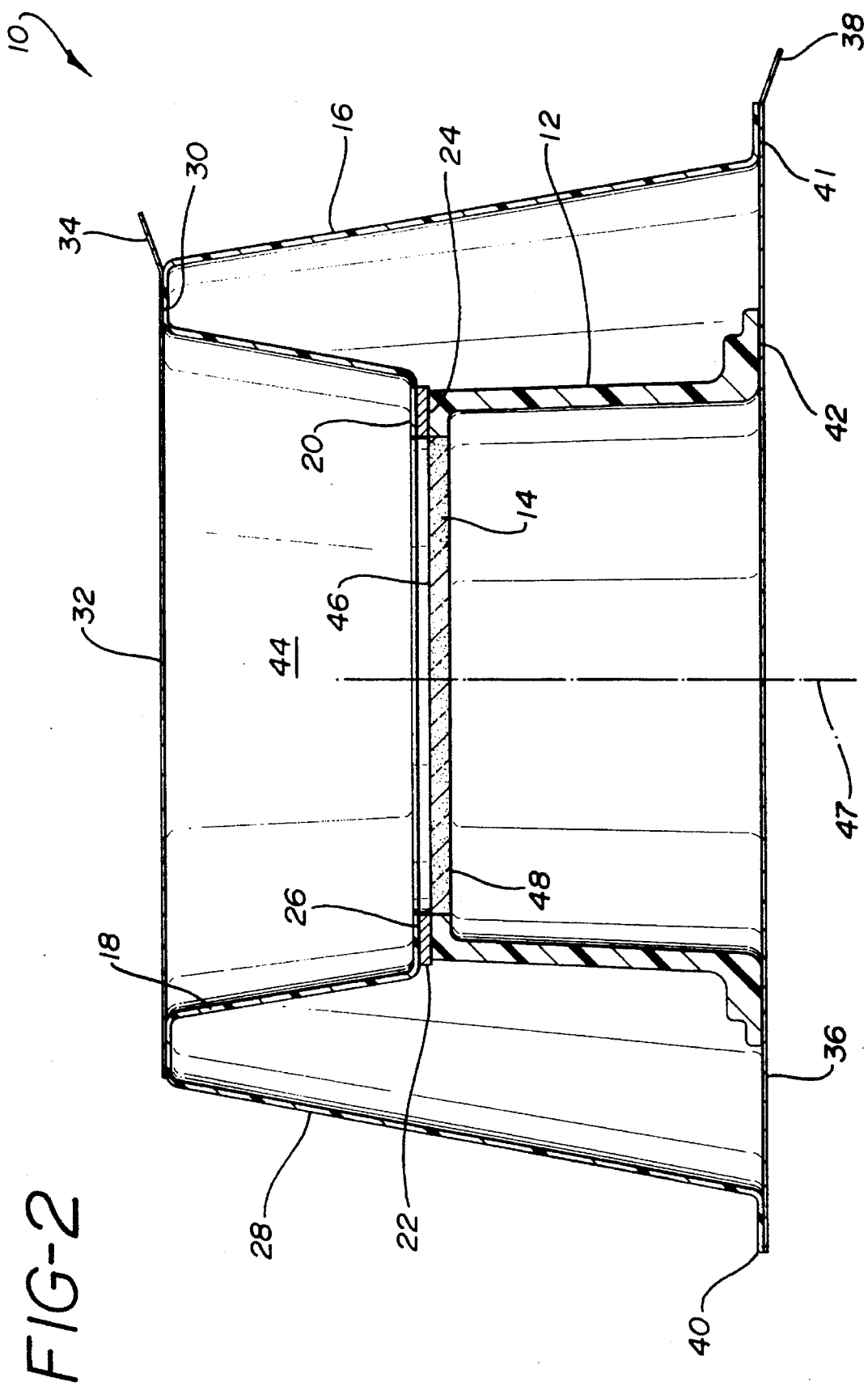

TRANSMEMBRANE CELL CULTURE DEVICE

This is a continuation of application Ser. No. 08/062,482 (now abandoned) filed on May 17, 1993, which is a continuation of U.S. Ser. No. 07/924,394, filed on Aug. 3, 1992 (now abandoned), which is a continuation of U.S. Ser. No. 07/665,383, filed on Mar. 6, 1991 (now abandoned).

BACKGROUND AND DESCRIPTION OF THE INVENTION

This invention relates to cell culture inserts for insertion into multi-well plates for culturing cells. More particularly, this invention relates to such inserts which have placed on the bottom surface thereof a microporous membrane as the substrate for cells being cultured. Even more particularly, this invention relates to such a cell culture insert device for supporting that insert in an inverted position initially so that cells may be developed on the bottom surface of the membrane of the support for subsequent interaction of developing cells on both the bottom and top surfaces of the porous membrane.

Initially, when cell inserts were developed for multi-well plates, they were comprised of a plastic material with an amorphous membrane material on the bottom surface thereof, for propagating cells. The inserts were placed in a conventional multi-well plate in the individual compartments therefore. However, in recent years, with the use of a suspended microporous membrane, two cell types for example, can be cultured, one on each side of the membrane in the same well. The microporous membrane allows free passage of macromolecules, proteins and ions. As a result, the interaction of the two cell types can be studied without actual physical contact between the two cell populations in the suspended state of the insert. The growth environment mimics the in vivo state of cells being developed in vitro and may replace in vivo testing which has taken place in the past.

As purely representative of materials which may be utilized for the microporous membranes in the device of the invention here, include, for example, polycarbonate and polyethylene terephthalate. The porosity of the membrane is developed to allow for selective permeation, as discussed above. The membrane material and/or the degree of porosity is developed to allow for direct viewing with phase contrast microscopy, as one feature of the use of such porous membranes. The membranes preferably are transparent or translucent.

As a further feature of this invention, it should be understood that the membrane porosity will be determined by specific applications. A representative porosity may be within the range of, for example, between about 0.2–10 microns.

As discussed above, and as a further background of the invention here, filter well culture on porous membrane substrates is growing in popularity because it provides a defined and reproducible culture environment that resembles the in vivo environment much more closely than ordinary cell culture conditions such as modified surfaces on petri dishes, for example. Some of the advantages include the ability to generate much higher cell densities, the possibility of establishing differentiated cell polarity, direct cell access to medium from below as well as from above, better gas exchange and the possibility of studying heterologous cell interactions that are mediated by diffusable substances.

This new and popular technology is used to enhance cellular differentiation, to study polarized ions and molecular transport across confluent epithelial monolayers, to more easily establish primary cell cultures, to study indirect i.e., diffusable substance-mediated cell interactions and to study the metastatic potential of malignant tumor cells.

Representative prior art includes U.S. Pat. No. 4,308,351 and is representative of current procedures now being used for cell culture inserts. U.S. Pat. No. 4,748,124 teaches a complex reusable culture chamber. Neither patent contemplates culturing on both sides of the same membrane.

In order to do this in the conventional way now, investigators are currently required to aseptically invert a conventional multi-well plate insert and try to establish a cell culture on the flat bottom surface of the membrane in a large drop of liquid medium whose depth is maintained only by surface tension on that flat surface. If these cells attach successfully, then the insert is inverted back to its normal orientation and placed into the multi-well plate containing a medium, wherein the second monolayer is then established inside the filter insert in the conventional manner.

It is to this problem that the present invention is directed so as to remove the improvised technique which often fails because of the compromised sterility or because the initial medium-and-cell droplet penetrates into the membrane too rapidly and/or evaporates prematurely.

Other objects and advantages of this invention will be apparent from the following description, the accompanying drawings and the appended claims.

DESCRIPTION OF THE INVENTION

FIG. 1 is an exploded, somewhat diagrammatic sectional view of the removable support device of the invention and its orientation with a conventional cell culture insert; and FIG. 2 is a view of the structure of FIG. 1 in its assembled configuration for initial use.

DETAILED DESCRIPTION OF THE INVENTION

Referring to the drawings in which like reference characters refer to like parts throughout the several views thereof, FIG. 1 shows the structure of the invention generally designated 10 having a conventional cell culture insert 12 inverted so that the porous membrane 14 of interest here is positioned on the upper surface as the cell culture insert 12 is oriented in FIG. 1. The invention includes an upper well support section 16 which includes an annular skirt 28 for supporting the entire structure. Skirt 28 is supported from a flat top surface 30 of the upper well section 16. Depending from upper flat surface 30 is an annular wall 18 which defines the initial cell culture compartment 44 of the support device of the invention. Preferably, upper well support 16 is a molded one-piece structure.

As can be seen in FIG. 1, the annular walls 18 defining the well 44 end in an annular flat lip or flange 20 which defines an opening for access to the top surface 46 of membrane 14 of cell insert 12. A gasket 22, which may have a double-sided adhesive, is utilized for joining the bottom surface 26 of the flange 20 with the top surface or membrane support flange 24 of cell culture insert 12. When this joining has taken place utilizing gasket 22, the upper chamber 44 properly surrounds and protects the surface 46 for cell propagation on porous membrane 14. 47 indicates the axis of structure 10.

Referring now to FIG. 2, the structure 10 is shown in its assembled position. In order to maintain sterility, a peelable lid 32 is positioned on the top annular surface 30 of the upper well section 16. The lid has a tab 34 for grasping the lid 32 for peeling it or removing it from top surface 30 when the structure is to be used for the initial propagation of a cell culture on surface 46 of porous membrane 14.

As can be seen in FIG. 2, a peelable lid 36 is adhered to the bottom surface 42 of cell insert 12, and the annular surface 41 of the flange 40 extending from the bottom surface of skirt 28 of the upper well section 16. This lid 36 also serves to maintain sterility until such time as the cell insert 12 is to be utilized for development of cell cultures on the surface 48 of membrane 14. As can be seen in FIG. 2, the lid or cover 36 also includes a tab 38 for grasping the cover 36 for peeling it from surfaces 41, 42 at the appropriate time during use.

Thus, the user takes the structure as shown in FIG. 2 and grasps the tab 34 and removes the cover or lid 32. Thereafter, the appropriate medium is applied to surface 46 and appropriate cell culturing takes place on surface 46 of membrane 14. Once appropriate propagation of cells has taken place on surface 46, the cover or lid 36 may be removed from the surfaces 41, 42 by grasping the tab 38.

Thereafter, the upper well section may be removed from the gasket 22 leaving the cell insert 12 with an initially developed cell culture on surface 46. The gasket 22 may then be removed from surface 24 and the insert 12 inverted and inserted into a well of a multi-well plate for subsequent conventional culturing of cells on surface 48.

Thus, as will be appreciated from the above, there is provided in accordance with this invention, a cell insert support arrangement with a separate disposable support for allowing the protection and support of a cell insert in its inverted position to allow for culturing of cells on the bottom surface of a porous membrane positioned on the cell insert. This is all achieved while maintaining the opposite surface of the porous membrane of the insert in a noncontaminated state for subsequent use.

Once the cells have been properly developed on the bottom surface of the porous membrane of the cell insert, the temporary structure of the invention may then be easily removed and disposed of so that the cell insert may be inverted while its internal well structure is still in its sterile state for subsequent cultivation of cells on the opposite surface of the porous membrane. This allows routinely for development of cultures on both sides of a porous membrane to enhance cellular differentiation, to study polarized (vectorial) ion and molecular transport across confluent epithelial monolayers, to more easily establish primary cell cultures, to study indirect cell interactions and to study other activities of cells such as the invasiveness of malignant tumor cells.

As practitioners-in-the-art will understand, the temporary throw-away support structures of the invention, as well as the conventional cell inserts themselves may be comprised of simple moldable parts which can be mass produced from a variety of materials, including, for example, polyethylene, polystyrene, polyethylene terephthalate and polypropylene. As will be understood further by practitioners-in-the-art, materials should be selected which will provide a small degree of resiliency for the purpose of providing ease of insertion of the inserts into multi-well plates and for appropriate handling during the cell culturing described above.

While the forms of apparatus herein described constitute preferred embodiments of the invention, it is to be understood that the invention is not limited to these precise forms of apparatus, and that changes may be made therein without departing from the scope of the invention which is defined in the appended claims. For example, whereas the form of insert shown and the temporary support structure shown is in cylindrical form, it should be understood that other configurations of inserts may be utilized in the form of square or rectangular configurations, depending upon the configurations of openings in the multi-well plates or other culture vessels being utilized, or as required by the user.

What is claimed is:

1. A support structure for use with a cell culture insert including a permeable membrane, comprising:

a longitudinal axis;

a top portion and a bottom portion;

an annular skirt extending from said top portion to said bottom portion and having an inner surface and an outer surface;

an inner inverted skirt portion, defining a culture chamber extending from said top portion to a lower portion and surrounded by said tuner surface of said annular skirt;

an annular flat lip having a top surface and a bottom surface on said lower portion of said inner inverted skirt;

a flange extending from said bottom portion of said annular skirt;

a gasket material comprising a double sided adhesive that is located on said bottom surface of said annular flat lip on said lower portion of said inverted skirt; and wherein said flat lip is spaced from said flange such that the culture insert is contained within the annular skirt when a bottom surface of the culture insert is attached to said gasket material.

2. A transmembrane cell culture system comprising:

a cell culture insert comprising an upper portion, a lower portion, a sidewall comprising an inner and outer surface and extending from said upper portion to said lower portion and a permeable membrane having an inside surface and a bottom surface and attached to said lower portion;

a support for accommodating the culturing of cells on a bottom side of said cell culture insert comprising:

a longitudinal axis;

a top portion and a bottom portion;

an annular skirt extending from said top portion to said bottom portion and having an inner surface and an outer surface;

an inner inverted skirt portion defining a culture chamber extending from said top portion to a lower portion and surrounded by said inner surface of said annular skirt;

an annular flat lip having a top surface and a bottom surface on said lower portion of said inner inverted skirt;

a flange extending from said bottom portion of said annular skirt;

a gasket material comprising a double sided adhesive that is located on said bottom surface of said annular flat lip on said lower portion of said inverted skirt;

wherein said annular flat lip mates with said lower portion of said cell culture insert so as to culture cells on said bottom surface of said permeable membrane; and wherein said flat lip is spaced from said flange such that the culture insert is contained within the annular skirt.

* * * * *